US012678208B2

(12) United States Patent
Medoff

(10) Patent No.: US 12,678,208 B2
(45) Date of Patent: **\*Jul. 14, 2026**

(54) METHOD AND APPARATUS FOR MAINTAINING A POSITION OF A BONE FRAGMENT IN RELATIONSHIP TO ANOTHER BONE PART

(71) Applicant: TriMed Inc., Santa Clarita, CA (US)

(72) Inventor: Robert Medoff, Kailua, HI (US)

(73) Assignee: TriMed, Inc., Santa Clarita, CA (US)

( \* ) Notice: Subject to any disclaimer, the term of this patent is extended or adjusted under 35 U.S.C. 154(b) by 90 days.

This patent is subject to a terminal disclaimer.

(21) Appl. No.: 18/651,019

(22) Filed: Apr. 30, 2024

(65) Prior Publication Data

US 2024/0277390 A1 Aug. 22, 2024

Related U.S. Application Data

(63) Continuation-in-part of application No. 17/152,253, filed on Jan. 19, 2021, now Pat. No. 11,986,227.
(Continued)

(51) Int. Cl.
A61B 17/80 (2006.01)
(52) U.S. Cl.
CPC ........ A61B 17/808 (2013.01); A61B 17/8004 (2013.01); A61B 17/8052 (2013.01)
(58) Field of Classification Search
CPC . A61B 17/0642; A61B 17/68; A61B 17/8004; A61B 17/809; A61B 17/842; A61B 17/848
See application file for complete search history.

(56) References Cited

U.S. PATENT DOCUMENTS

| 1,130,378 A | 3/1915 | Collis |
| 2,501,978 A | 3/1950 | Wichman |
| | (Continued) | |

FOREIGN PATENT DOCUMENTS

| CN | 209 529 310 U | 10/2019 |
| GB | 2 451 187 A | 1/2009 |

OTHER PUBLICATIONS

Extended European Search Report issued Apr. 25, 2023 in European Patent Application No. EP 21 74 4471.
(Continued)

*Primary Examiner* — Larry E Waggle, Jr.
(74) *Attorney, Agent, or Firm* — Wood, Phillips, Katz, Clark & Mortimer

(57) ABSTRACT

A method and apparatus for maintaining a position of a first bone part relative to a second bone part. The method includes the steps of: a) obtaining an apparatus having a base in the form of a plate and at least one elongate wire component having at least a portion with a length projecting angularly away from the base; b) placing the apparatus in an operative position wherein at least a portion of the length of the at least one elongate wire component engages the first bone part and a portion of the base at least one of: i) bears against; and ii) is adjacent to the second bone part; and c) with the apparatus in the operative position, anchoring the base to the second bone part to fix the apparatus in the operative position. At least a part of the base and at least a part of the at least one elongate wire component are made from metal and permanently connected.

25 Claims, 8 Drawing Sheets

Related U.S. Application Data

(60) Provisional application No. 62/963,330, filed on Jan. 20, 2020.

(56) References Cited

U.S. PATENT DOCUMENTS

| | | | |
|---|---|---|---|
| 5,352,229 | A | 10/1994 | Goble et al. |
| 5,586,985 | A * | 12/1996 | Putnam ................. A61B 17/809 |
| | | | 606/904 |
| 5,709,682 | A | 1/1998 | Medoff |
| 5,718,706 | A | 2/1998 | Roger |
| 5,779,707 | A | 7/1998 | Bertholet et al. |
| 5,941,878 | A | 8/1999 | Medoff |
| 5,961,521 | A | 10/1999 | Roger |
| 6,113,603 | A | 9/2000 | Medoff |
| 6,432,140 | B1 | 8/2002 | Lin |
| 7,037,308 | B2 * | 5/2006 | Medoff .............. A61B 17/7208 |
| | | | 606/151 |
| 7,731,718 | B2 | 6/2010 | Schwammberger et al. |
| 7,811,286 | B2 | 10/2010 | Medoff |
| 7,942,301 | B2 | 5/2011 | Sater |
| 7,942,877 | B2 | 5/2011 | Medoff |
| 7,988,691 | B2 | 8/2011 | Schulze et al. |
| 8,235,995 | B2 | 8/2012 | Focht et al. |
| 8,287,543 | B2 | 10/2012 | Medoff |
| 8,337,528 | B2 | 12/2012 | Ferree |
| 8,475,504 | B2 | 7/2013 | Gillard et al. |
| 8,617,214 | B2 | 12/2013 | Malek |
| 8,795,277 | B2 | 8/2014 | Leuenberger et al. |
| 9,089,378 | B2 * | 7/2015 | Riemer ................ A61B 17/842 |
| 9,427,232 | B2 | 8/2016 | Gupta et al. |
| 9,433,452 | B2 | 9/2016 | Weiner et al. |
| 9,603,597 | B2 | 3/2017 | Gupta et al. |
| 9,737,337 | B2 | 8/2017 | Ferree |
| 10,004,603 | B2 | 6/2018 | Appenzeller et al. |
| 11,986,227 | B2 * | 5/2024 | Medoff .............. A61B 17/8052 |
| 2006/0189992 | A1 | 8/2006 | Medoff |
| 2007/0233113 | A1 | 10/2007 | Kaelblein et al. |
| 2008/0077132 | A1 | 3/2008 | Medoff |
| 2009/0069851 | A1 | 3/2009 | Gillard et al. |
| 2014/0012316 | A1 | 1/2014 | Stupak |
| 2014/0058510 | A1 | 2/2014 | Appenzeller et al. |
| 2016/0367298 | A1 | 12/2016 | Weiner et al. |
| 2018/0263778 | A1 | 9/2018 | Appenzeller et al. |
| 2019/0357953 | A1 | 11/2019 | Venturini et al. |
| 2020/0008846 | A1 | 1/2020 | Medoff |

OTHER PUBLICATIONS

International Preliminary Report on Patentability and Written Opinion of the International Searching Authority, issued Jul. 26, 2022 in International Patent Application No. PCT/US2021/013938.

* cited by examiner

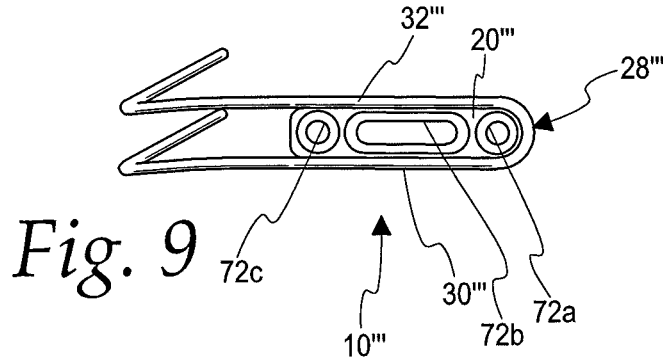
*Fig. 9*
*Fig. 10*
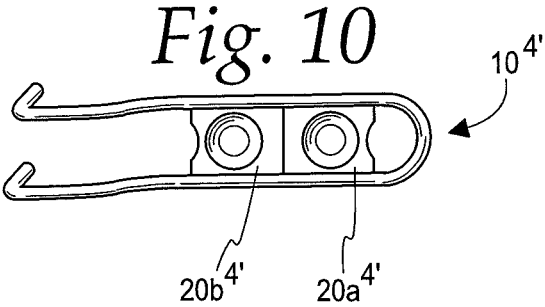
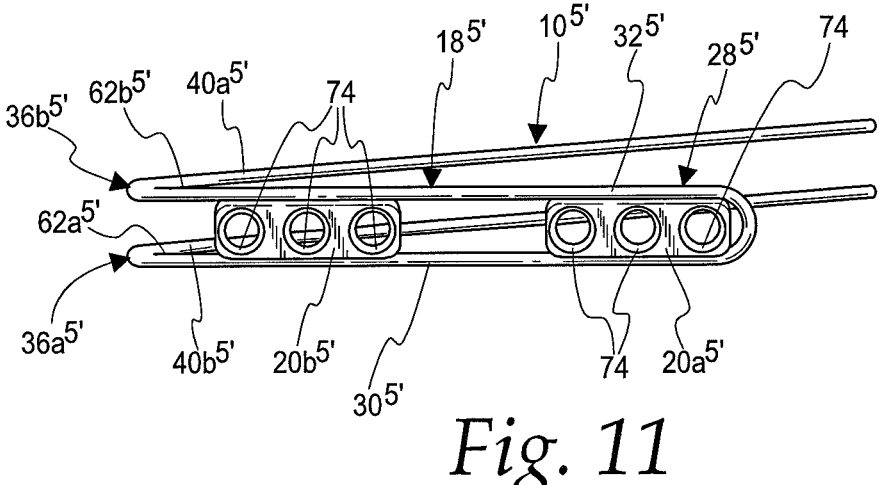
*Fig. 11*

METHOD AND APPARATUS FOR MAINTAINING A POSITION OF A BONE FRAGMENT IN RELATIONSHIP TO ANOTHER BONE PART

CROSS REFERENCE TO RELATED APPLICATIONS

This application is a continuation-in-part of U.S. patent application Ser. No. 17/152,253, filed Jan. 19, 2021, which claims priority to U.S. Provisional Patent Application No. 62/963,330, filed Jan. 20, 2020.

BACKGROUND OF THE INVENTION

Field of the Invention

This invention relates to medical implants and, more particularly, to a method and apparatus used to maintain a desired relationship between separate bone parts, such as a bone fragment and another stabilizing bone part.

Background Art

Many different implants have been devised to maintain a desired position of a bone fragment in relationship to another bone part, which may be an uncompromised stable bone part or another intermediate fragment. For simplicity, maintenance of a relationship between a bone fragment and a "stable" bone part will be focused upon herein only as a representative practicing of the invention. However, the invention more generically relates to controlling a relationship between any separate bone parts.

One category of this type of implant uses a formed wire arrangement that is fixed to a stable bone part. The wire portion generally either captively holds a separated bone fragment in a desired relationship or provides a foundation upon which a "bone fragment" can be effectively constructed.

For purposes of simplicity throughout the background, description, and claims herein, a "formed elongate component or wire" will be used generically to encompass an actual wire, a pin, and any other like elongate component that is strategically shaped to function as other than a straight piece or fastener. For each implant, the wire is shaped to accomplish a specific task, based upon the particular anatomy—including the particular bone that is stable and the nature of the fragment to be maintained in a desired relationship therewith. Currently, such wires are commonly made from 0.045" to 0.090" diameter material, though other gauges are utilized.

The Applicant herein makes a number of such implants, certain of which have been arbitrarily identified as "sled" implants, with others characterized as buttressing devices. A number of such representative apparatus are disclosed in the following patents, assigned to the Applicant herein: U.S. Pat. No. 5,709,682 ("Surgical Clamp For Fixation Of Bone Fragments"); U.S. Pat. No. 5,941,878 ("Implantable Surgical Buttressing Device"); U.S. Pat. No. 6,113,603 ("Graft Constraint Device"); U.S. Pat. No. 7,037,308 ("Implant Device For Applying Compression Across A Fracture Site"); U.S. Pat. No. 7,811,286 ("Implant Device For Applying Compression Across A Fracture Site"); and U.S. Pat. No. 8,287,543 ("Fracture Fixation System Including Buttress Pin And Post Washer").

The diameter of the wires can be constant or non-uniform. In a typical configuration, the wire has a proximal U-shaped portion that is fixed to a stable bone part and extends to one or more legs, each with a free end. In some configurations, the U-shaped portion has a smaller gauge to facilitate formation, as well as provide a low profile on the surface of the bone, with the legs having a larger gauge for strength and rigidity.

Heretofore, these wire forms have been secured to bone by applying a washer or small plate, hereinafter generically identified as a "washer". The washer is placed on the wire surface to sandwich the implant between the undersurface of the washer and the underlying bone.

While this construction has been functional, there are a number of undesirable features inherent with this design. First, it is somewhat awkward and inconvenient for a surgeon to have to handle separate pieces—in this case the washers, fasteners, and implant body—during a procedure. A surgeon must coordinate the handling of the pieces to allow fastener-accommodating holes to be drilled into the bone. In the case of a small diameter wire, a commonly used washer is proportionately small and difficult to handle, and thus prone to being dropped during a procedure-which, aside from the inconvenience, creates the potentially difficult task of recovering and repositioning the same. For example, one known washer has been designed to be quite small to ensure that it does not cover a large surface of bone and thereby limit screw placement from an opposite side. However, it is easy for this washer to rotate under the wire body, as a result of which it may become awkward to reorient the same.

With certain of Applicant's "sled" and buttress-type implants, it may be necessary to drill two or three holes, and it is thus important that the surgeon not shift the position of the washer as holes are serially drilled.

Further, fixation of the implant is dependent upon the amount of clamping force between the washer and the bone. It may not be possible to consistently develop an optimal clamping force in all applications. For example, in the case of small wire forms, if any resorption occurs under the washer, the clamping force may be diminished. Further, in some cases, the bone is osteoporotic and sufficient force may not be generated due to stripping of the thread in the bone.

In certain applications, the region of the stable bone where the implant is fixed is not flat underlying the region where the washer overlies the wire form. As a result, the washer may not compress against the bone on opposite sides of the implant, whereby inadequate fixation may result. This condition is encountered, for example, with the Applicant's "olecranon sled" implant.

Applicant has developed washers that can be snapped onto a wire form, thereby with the objective of avoiding the difficulty in the handling and applying of separate washers during a surgical procedure. The precision required to allow positive maintenance of the washer on different wire forms makes the commercial production of this type of implant challenging. Even slight deviations from dimensional tolerances could compromise fixation of the implant. Further, this design may not solve the problem associated with forcibly sandwiching the wire form between the washer and bone.

Still further, a captive washer arrangement stacks component thicknesses which could result in patient discomfort, with potential tissue irritation and even damage.

The challenge to continue to improve this basic implant design, to better address one or more of the above areas, continues to exist in the medical industry.

SUMMARY OF THE INVENTION

In one form, the invention is directed to a method of maintaining a position of a first bone part relative to a second bone part. The method includes the steps of: a) obtaining an apparatus having a base in the form of a plate, and at least one elongate wire component having at least a portion with a length projecting angularly away from the base; b) placing the apparatus in an operative position wherein at least a portion of the length of the at least one elongate wire component engages the first bone part and a portion of the base at least one of: i) bears against; and ii) is adjacent to the second bone part, and as an incident of placing the apparatus in the operative position, causing at least a portion of the elongate wire component to be deformed so that residual forces are generated in the elongate wire component; and c) with the apparatus in the operative position, anchoring the base to the second bone part to fix the apparatus in the operative position. At least a part of the base and at least a part of the at least one elongate wire component are made from metal and permanently connected.

In one form, the plate is substantially flat.

In one form, the plate is made from flat stock material.

In one form, at least a portion of the at least part of the base and a portion of the at least part of the elongate wire component are formed as one piece.

In one form, the plate has a substantially flat surface that faces the second bone part with the apparatus in the operative position. The length of the portion of the at least one elongate wire component projects angularly with respect to the substantially flat surface of the plate.

In one form, the step of placing the apparatus in the operative position involves causing the at least portion of the length of the at least one elongate wire component to be directed into the first bone part.

In one form, the at least one elongate wire component defines a U-shaped receptacle. With the apparatus in the operative position, at least a part of the first bone part resides in the U-shaped receptacle.

In one form, the U-shaped receptacle is defined by the at least one elongate wire component.

In one form, the U-shaped receptacle is defined by the at least one elongate wire component in conjunction with the base.

In one form, the at least one elongate wire component includes additionally a second elongate wire component having a length portion projecting angularly away from the base. At least a portion of the second elongate wire component is formed as one piece with at least a portion of the at least part of the base and a portion of the at least part of the at least one elongate wire component.

In one form, the step of anchoring the base involves directing a fastener through the base and into the second bone. The step of directing the fastener involves camming the base with the fastener so that at least a portion of the residual forces are lengthwise forces in the at least portion of the elongate wire component that urge the first bone part towards the second bone part.

In one form, the invention is directed to an apparatus for maintaining a position of a first bone part relative to a second bone part. The apparatus has a unitary body made up of: a) at least one elongate wire component; and b) a plate that has a first surface. A length of at least a portion of the at least one elongate wire component is angled with respect to the first plate surface. At least a part of each of the at least one elongate wire component and plate is made from metal. The at least one elongate wire component is permanently fixed to the plate. The apparatus is configured to be: a) placed in an operative position with the length of the at least part of the elongate wire component engaged with the first bone part and the first surface of the plate facing the second bone part;

and b) maintained in the operative position by fixing the plate to the second bone part. At least a part of the elongate wire component is configured to be deformed as an incident of the apparatus being placed in the operative position so that residual forces are generated in the at least one elongate component.

In one form, at least a portion of the at least part of the plate is formed as one piece with at least a portion of the at least one elongate wire component.

In one form, the plate is made from flat stock material.

In one form, the plate has a second surface facing oppositely to the first surface. The at least one elongate wire component is welded to the plate at each of the first and second surfaces.

In one form, the at least one elongate wire component is welded to the plate at one of the first and second surfaces continuously along a length.

In one form, the at least one elongate wire component is welded to the plate along a length at each of the first and second surfaces.

In one form, the portion of the plate is laser welded to a portion of the at least one elongate wire component.

In one form, the at least one elongate wire component defines a U-shaped receptacle into which at least a part of the first bone part resides with the apparatus in the operative position.

In one form, the U-shaped receptacle is defined by the at least one elongate wire.

In one form, the U-shaped receptacle is defined by the at least one elongate wire in conjunction with the plate.

In one form, the apparatus is provided in combination with a fastener configured to be directed through the plate and into the second bone to maintain the apparatus in the operative position.

In one form, the at least one elongate wire component includes additionally a second elongate wire component having at least another portion with a length. The length of the at least another portion of the second elongate wire component is angled with respect to the plate surface.

In one form, the plate is formed from a flat stock material.

In one form, the unitary body includes a second plate.

BRIEF DESCRIPTION OF THE DRAWINGS

FIG. 9 is a top, perspective view of still another form of the inventive apparatus, as shown in FIG. 1;

FIG. 10 is a top, perspective view of a further modified form of the inventive apparatus, as shown in FIG. 1;

FIG. 11 is a top, perspective view of a still further modified form of the inventive apparatus, as shown in FIG. 1;

DETAILED DESCRIPTION OF THE PREFERRED EMBODIMENT

Figures 1, 2, 3:
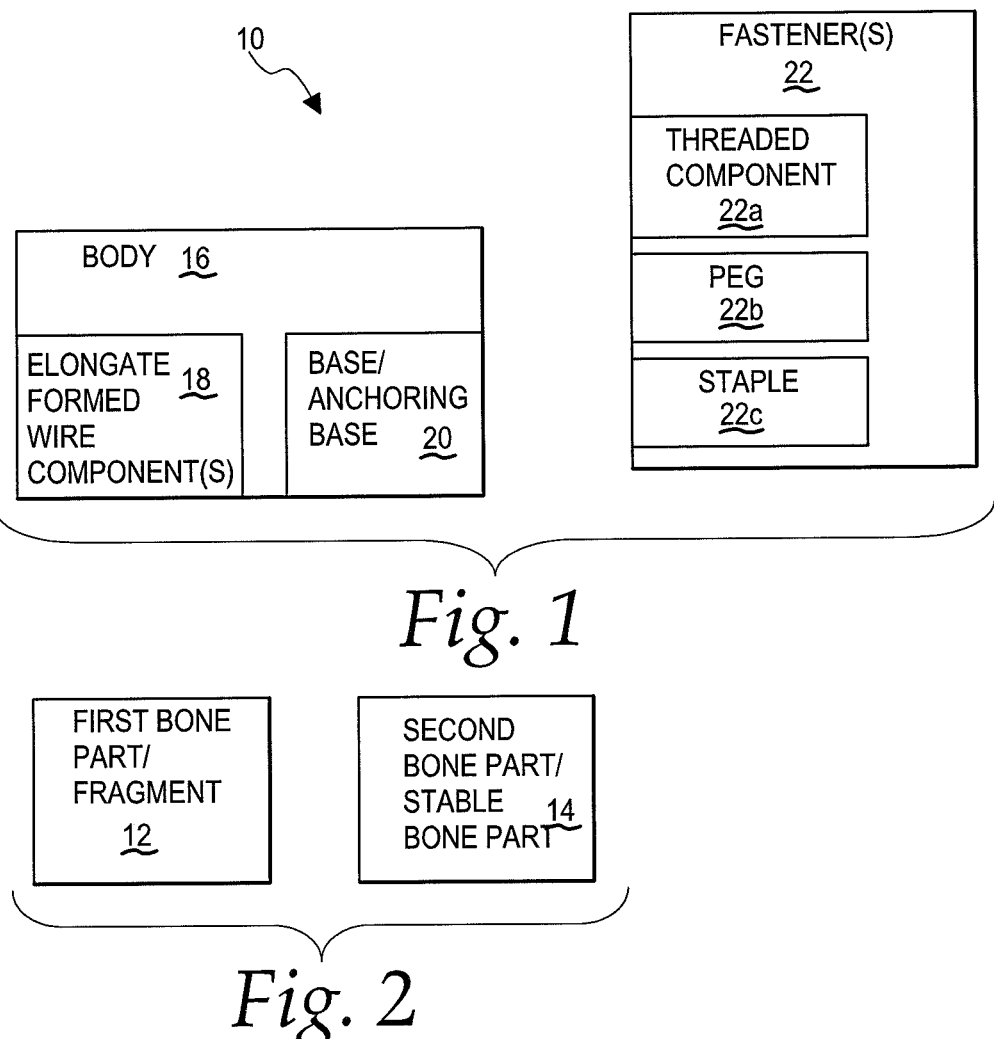
FIG. 1 is a schematic representation of an apparatus for maintaining a position of a first bone part in relationship to a second bone part, according to the invention.
FIG. 2 is a schematic representation of exemplary first and second bone parts identified respectively as a bone fragment and a stable bone part.
FIG. 3 is a schematic representation showing further details of a unitary body on the inventive apparatus in FIG. 1.

In FIG. 1, an apparatus in the category to which the present invention is directed is shown schematically at 10. The apparatus 10 defines an implant that is usable to maintain the position of a first bone part/fragment 12, as shown in FIG. 2, in relationship to a second bone part/stable bone part 14. The apparatus 10 is of the type that can be used in association with many different bones, as encompassed by the generic showing in FIG. 2.

Exemplary applications for this type of apparatus 10 are disclosed in the Applicant's various patents listed above. The disclosure in each of these patents is incorporated herein by reference. It should be understood that the different applications described therein are not to be viewed as limiting, as the invention can be practiced with virtually any bone parts, regardless of their nature or number, which are to be maintained in a desired relationship.

The apparatus 10 in FIG. 1 consists of a unitary body 16 made up of at least one elongate formed wire component 18 and a base/anchoring base 20 that may be made up of a single piece or multiple pieces.

As used throughout the description herein, a "unitary body" is a body made up of a single piece or multiple pieces that are permanently secured together in a fixed relationship to function as one piece.

The base 20 is configured to directly or indirectly cooperate with at least one fastener 22 that can be used to maintain the apparatus 10 in an operative position relative to the bone parts 12, 14. The generic showing of the fastener 22 is intended to encompass any fastener that cooperates between the base 20 and the second bone part 14 to thereby fix the base 20 to the second bone part 14.

Within the generic showing in FIG. 1 are an exemplary threaded component/screw 22a, a peg 22b, and a staple 22c. These examples are not all-inclusive of the fasteners contemplated. Within the generic showing of the fastener 22 is also any structure that might clamp the base 20 in place relative to the second bone part 14.

The formed wire component is configured to engage at least the first bone part 12, and potentially the second bone part 14, with the apparatus 10 in an operative position, which operative position is maintained by using one or more appropriate fasteners 22 to fix the base 20 to the second bone part 14.

In FIG. 3, one exemplary form of unitary body 16 is shown in further detail. The elongate formed wire component 18 has a first length portion 24 that is coextensive with, placed against, and fixed relative to a portion 26 of the base 20. In another form, this same configuration may be defined by a single piece. The portion 26 may be any part of the base 20 and in one exemplary form is on a peripheral edge of the base 20.

As noted above, the bone part 12 may be a bone fragment formed by a fracture of the bone defining the second bone part 14. The generic showing is also intended to encompass any apparatus 10 that serves as a foundation for a bone fragment 12 that is at least partially constructed, as by a grafting process.

As noted above, the generic showing of the elongate formed wire component 18 is not limited to any particular shape or diameter. Further, while a single wire is shown in each apparatus herein, multiple wire pieces could be utilized to produce the same or similar shapes. The generic showing is intended to encompass any elongate component that is of uniform or varying diameter that is strategically shaped and placed to facilitate retention of the first bone part 12 relative to the second bone part 14, be it by defining a receptacle for the first bone part 12, bearing against a surface of the first bone part, and/or by penetration thereof.

Without limitation, exemplary forms of the elongate formed wire component 18 are shown in the aforementioned patents, incorporated herein by reference.

As noted above, the elongate formed wire component 18 may have a substantially constant diameter or may vary in diameter. Commonly, the cross-sectional shape will be substantially circular, however this is not required. As one example, the diameter may be on the order of 0.045 to 0.090 inches. The diameter of the elongate formed wire component 18 may be slightly greater where there is connection to the base 20 to add greater stability and reduce elasticity, while having a stepped or tapered diameter therefrom. Alternatively, a smaller diameter at the base connection may facilitate formation and result in a more compact design. Regions that are bent may have a locally reduced diameter to facilitate formation. The formed portions extending away from the base 20 may have a larger diameter to exhibit the necessary strength and resistance to bending while potentially being semi-elastic in nature to allow some adaptation to conditions at different surgical sites.

Similarly, the generically depicted base 20 is not limited in terms of its construction. As noted, the base 20 may be made up of one or more parts that can be suitably fixed relative to the second bone part 14. Each base part may be made substantially flat or may be contoured to conform to the patient's anatomy at the operating site. The plate shapes may have a uniform thickness or varying thickness.

For purposes of simplicity, the exemplary bases described herein will be shown fixed relative to the second bone part by a fastener that extends through the base 20 to purchase bone thereunder or thereadjacent. As noted, this construction is not required.

Typically, the elongate formed wire component(s) 18 and base 20 will be made from a medical grade material. In the event that the unitary body 16 is made from separate parts that are united, such process typically will be accomplished by welding. With metal components, typically a laser welding process is utilized.

Further, permanent connection may also be accomplished through a permanent bonding process, including, but not limited to, one utilizing adhesives or fused materials. As one example, plastic material may be ultrasonically bonded to the metal of the formed wire component 18. Further, interdigitation of one material to another, such as, but not limited to, a porous surface on another, etc. might be practiced.

The invention also contemplates formation of the unitary body from a single piece of material. Alternatively, a single piece may define part of the base 20 and part of the elongate formed wire component 18, or the entirety of one of the base 20 and elongate formed wire component 18 and only part of the other of the base 20 and elongate formed wire component 18.

Figures 4, 5:
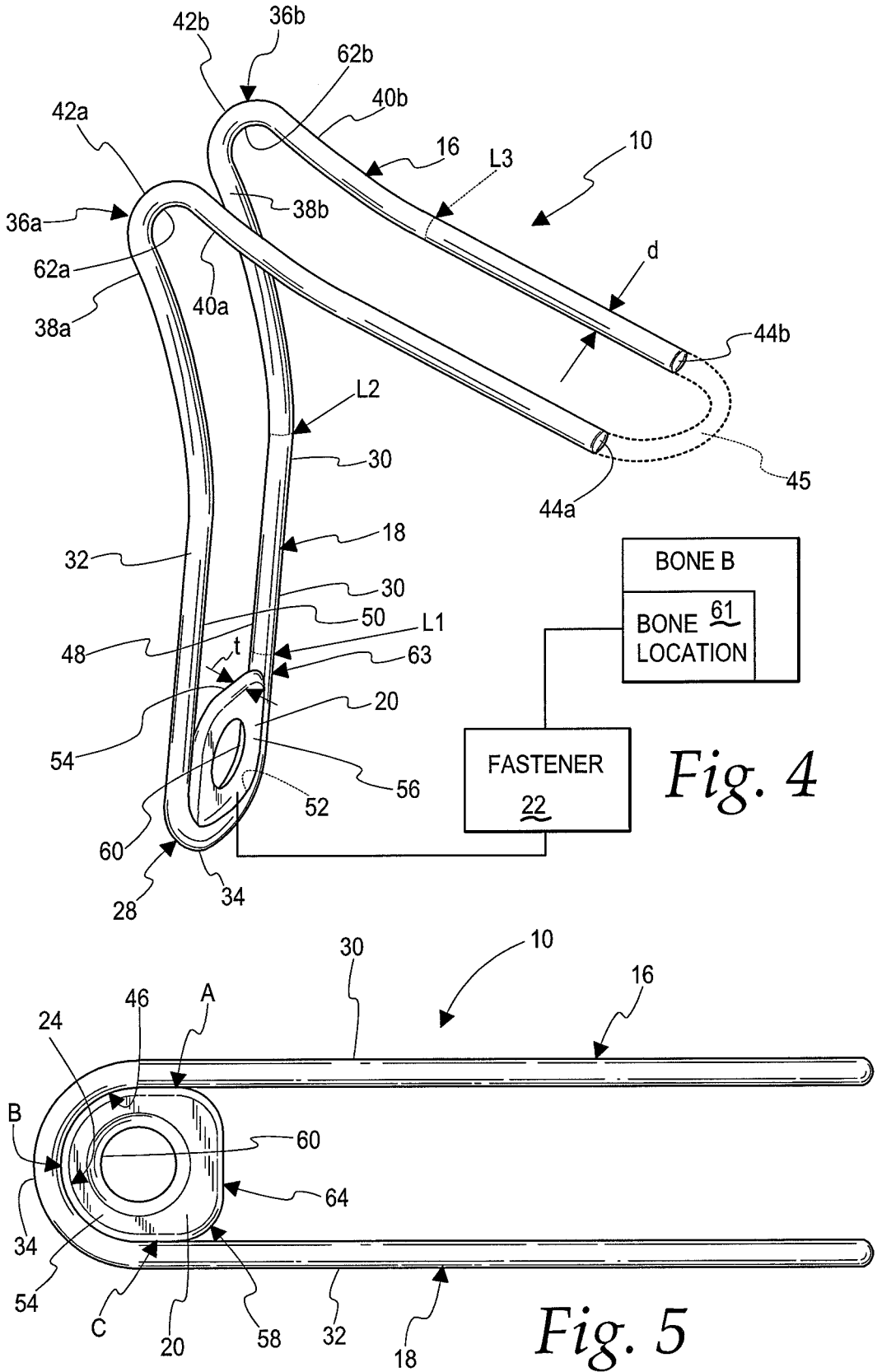
FIG. 4 is a bottom perspective view of one specific form of the inventive apparatus, as shown schematically in FIG. 1.
FIG. 5 is a plan view of the apparatus in FIG. 4.

Exemplary forms of the invention will now be described. In FIGS. 4 and 5, one exemplary form of the apparatus 10 is shown that incorporates a buttressing capability. In this embodiment, the body 16 consists of a single, elongate formed wire component 18. The elongate formed wire component 18 has a U-shaped mounting portion 28 defined by legs 30, 32 projecting in spaced relationship away from a base/base portion 34.

The leg 32 extends to define a separate U-shaped portion 36a with spaced legs 38a, 40a projecting away from a base 42a. The leg 30 extends into a like form, including a U-shaped portion 36b with legs 38b, 40b projecting away from a base 42b.

The legs 40a, 40b coextend in spaced relationship from respective bases 42a, 42b to unconnected free ends 44a, 44b. The free ends 44a, 44b in this buttressing configuration, and corresponding free ends in other embodiments herein, may be connected by making the legs 40a, 40b contiguous with each other or by using a separate element 45, as shown in dotted lines in FIG. 4. For purposes of simplicity the leg ends 44a, 44b will be considered "free ends", whether or not connected to each other.

In this embodiment, the base 20 is in the form of a flat plate and nests conformingly within a U-shaped receptacle 46 defined on the U-shaped mounting portion 28 by facing leg edges/surfaces 48, 50, respectively on the legs 30, 32, and an edge/surface 52 on the base 34 connecting between the edges/surfaces 48, 50.

The base/plate 20 has oppositely facing surfaces 54, 56 that in this embodiment are substantially parallel so that the base/plate has a substantially uniform thickness t. As noted, contoured surfaces may be utilized to conform to an underlying bone. The flat shape facilitates formation from a flat stock material.

By conforming a peripheral edge 58 on the base/plate 20 to the edges/surfaces 48, 50, 52, a solid foundation is defined that affords a region of potentially high strength and rigidity.

The portion of the elongate formed wire component 18 that is coextensive with, against, and fixed relative to the peripheral edge 58 corresponds to the first length portion 24, as identified schematically in FIG. 3.

The first length portion 24 may be unitarily joined with the peripheral edge 58 over its entire length, as by welding, adhesive, etc. Welding is preferred to establish a permanent positive connection.

Alternatively, the first length portion 24 can be fixed to the peripheral edge 58 at discrete, spaced locations, with representative locations being identified at A, B, and/or C. In this case a weld is made between the base 20 and each of the legs 30, 32 and base 34.

Separate welds may be made at each, or any, of the locations A, B, C with one of the separate welds closer to, or at, the surface 54, and the other of the separate welds closer to, or at, the surface 56.

As noted, this same, or a similar, basic configuration might alternatively be formed as a single piece.

Once the unitary body 16 is defined, it can be fixed in its operative position. To accomplish this, the base 20 is provided with a single, fully surrounded opening 60 through which a fastener 22 can be extended into a bone or bones, generically identified at B, at a bone location 61.

With this configuration, typically the legs 40a, 40b will be directed into the first bone part 12. Alternatively, or in addition to this penetration, the U-shaped portions 36a, 36b respectively define receptacles 62a, 62b that individually or cooperatively engage the first bone part 12 which has at least a part that is at least nominally matched to the shape thereof to allow a captive arrangement to be established.

In this embodiment, the apparatus can perform both a captive function and a buttressing function, depending upon the particular bone and the condition thereof.

As depicted, the diameter of the elongate formed wire component 18, identified as d, is substantially uniform along its entire length. Alternatively, different diameters might be strategically selected as to facilitate formation and/or provide controlled rigidity at different parts of the apparatus 10. A typical diameter for the elongate formed wire component 18 is in the range of 0.045 inches to 0.090 inches. This diameter is not limiting, as it is contemplated that the diameter could be substantially greater than 0.090 inches or less than 0.045 inches.

The relationship of the "bottom" surface, that directly overlies the bone, and the bone at the anchoring location is not limited. The elongate formed wire component 18 and base/plate 20 may be joined/formed in different manners and may have different shapes and dimensional relationships depending upon the particular application.

In one form, the bottom plate surface 56 is flush with the bottom edge 63 defined by the U-shaped mounting portion 28 so that the surface 56 and edge 63 seat simultaneously against a complementarily-shaped bone surface. The plate surface 56 may extend to below the bottom edge 63 to be the primary bone contacting surface in the vicinity of the fastener 22.

Alternatively, the surface 56 can be slightly above the edge 63, whereby drawing of the base/plate 20 towards the bone location 61 bears at least part of the edge 63 positively against the bone before the surface 56 makes engagement. Alternatively, the surface 56 may be maintained above the bone B at the location 61.

In one preferred form, the thickness t of the base/plate 20 is less than the diameter d for the elongate formed wire component 18, whereby the base/plate surfaces 54, 56 can reside within the diameter d of the elongate formed wire component 18. As noted, the diameter d may be greater than or equal to the thickness t.

With the surface 56 spaced slightly from the bone at the location 61, a residual biasing force may be imparted to the base/plate 20 through a securing fastener 22, which may contribute to a more positive connection.

A slight downward recess of the base/plate surface 54 from the top edge of the U-shaped mounting portion 28 defined by the elongate formed wire component 18 may avoid localized projection that could irritate overlying tissue.

As depicted, the legs 40*a*, 40*b* coextend in spaced relationship and terminate at the free ends 44*a*, 44*b*, respectively. However, this coextension is not required and potentially part or all of one of the legs 40*a*, 40*b* might be changed in shape or length in relationship to the other, or altogether eliminated. As shown in FIG. 4, the apparatus 10 might be changed by eliminating part of the leg 30, as shown in dotted lines at alternative locations L2, L3, or all or substantially all of the leg 30 as shown in dotted lines at L1. These are just examples of virtually an unlimited number of different variations that might be made. Further, the matching shape, and substantially parallel relationship over the coextension of the legs 30, 32 is not required.

The legs 32, 40*a* and legs 30, 40*b* can also be considered to be each separately making up the U-shaped portions 36*a*, 36*b*, with the legs 32, 30 fixed to the base/plate 20 and the legs 40*a*, 40*b* extending to the free ends 44*a*, 44*b*, respectively.

As noted above, the elongate formed wire component 18 may have a uniform diameter d. Alternatively, different length portions may have different diameters. For example, the length portions defined by the legs 40*a*, 40*b* may have a diameter different than the first length portion 24, or the same diameter. The former construction potentially facilitates bending of the U-shaped portion connected to the base/plate 20 while allowing portions other than the first length portion 24 to be more rigid for greater integrity and resistance to bending.

As shown in the drawings, as with all embodiments herein, all exposed edge regions 64 on the base/plate 20 are rounded to avoid tissue irritation.

Figure 6:
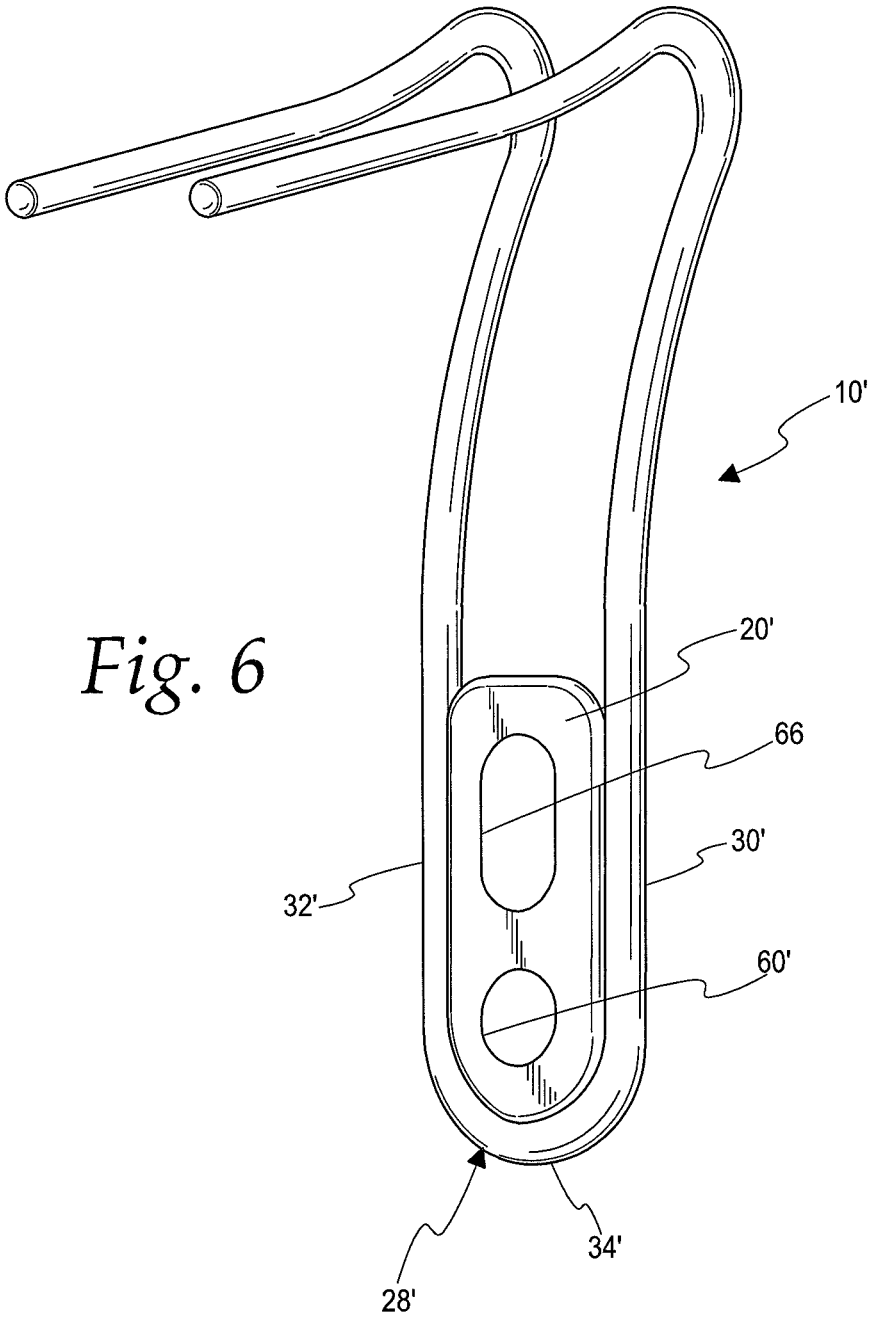
FIG. 6 is a bottom perspective view of a further modified form of the inventive apparatus, as shown in FIG. 1.
Figure 7:
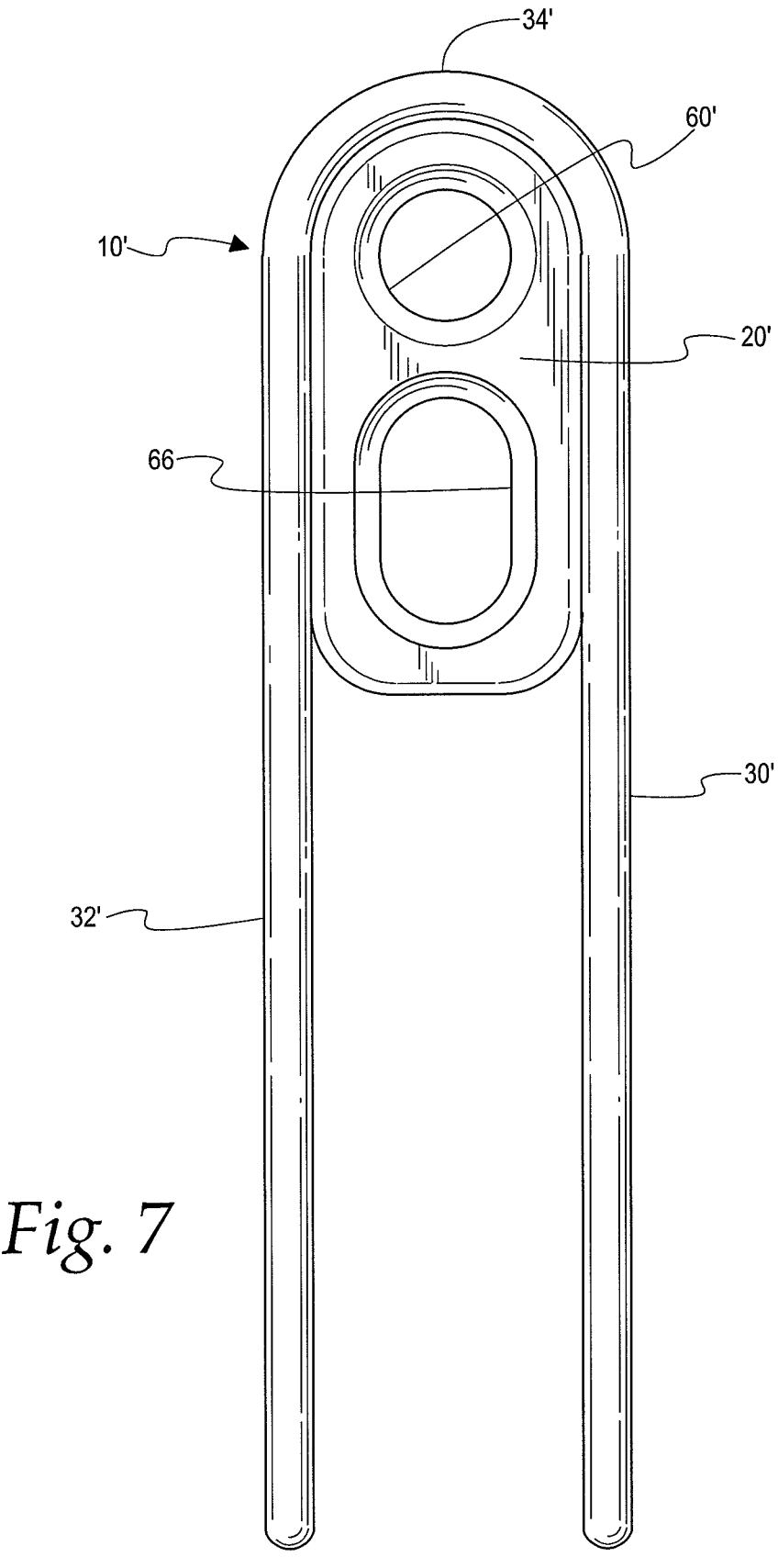
FIG. 7 is a plan view of the apparatus in FIG. 6.

In FIGS. 6 and 7, a modified form of the apparatus is shown at 10', which apparatus is substantially the same as the apparatus 10, with the primary distinction being that the corresponding base 20' extends away from the base 34' of the U-shaped mounting portion 28' further along the length of the legs 30', 32'. The extended base configuration provides an increased area to form an elongate/oval opening 66, in addition to the opening 60'. The opening 66 accepts a corresponding fastener 22 and allows a fastener 22 to be directed therein at different locations. This permits more strategic placement of a fastener and/or allows guided relative movement to occur between the apparatus 10' and the bone, as before a separate fastener 22 is directed through the opening 60' to fix a precise position.

In this embodiment, the base 20' is shown with a substantial flat shape and overall length and width areal dimensions that produce an overall square shape. The substantially uniform width depicted rigidifies the portions of the elongate formed wire component projecting in parallel relationship away therefrom.

As depicted, both of the openings 60', 66 are fully surrounded by the plate/base 20'. However, it is not necessary that the base/plate 20' fully surround both, or either, of the openings 60', 66.

The apparatus 10', as all apparatus 10 herein, may be formed by separately united parts or as one piece.

Figure 8:
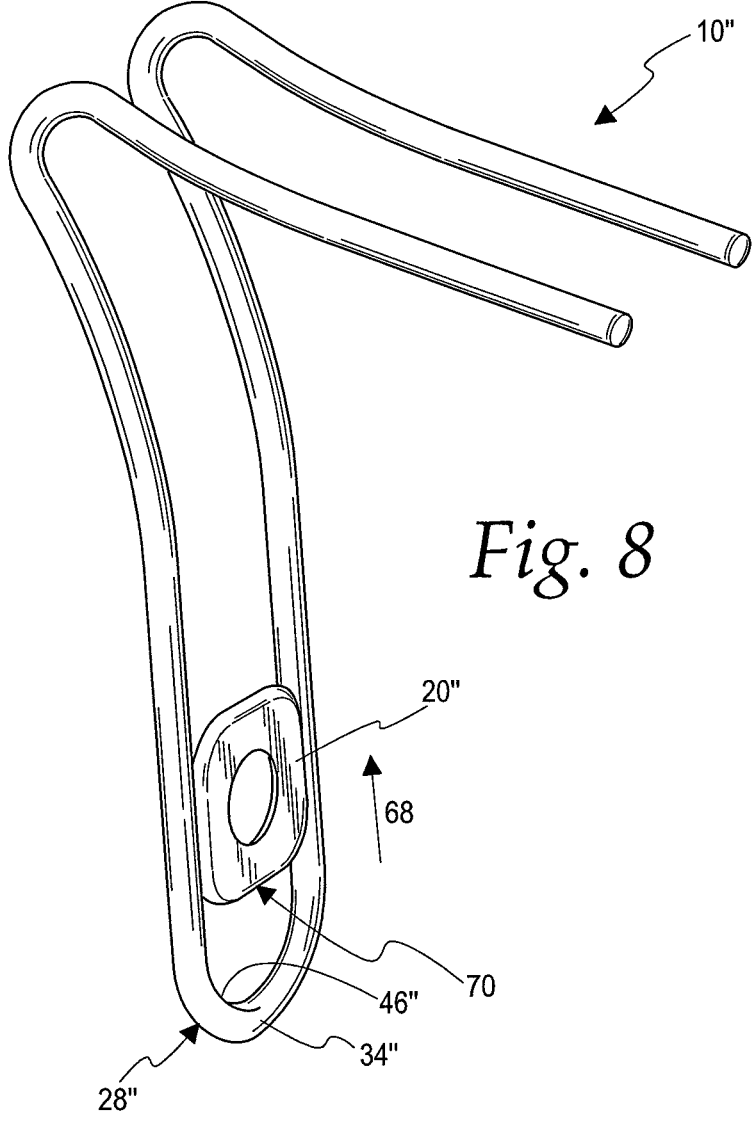
FIG. 8 is a bottom perspective view of a further modified form of the inventive apparatus, as shown in FIG. 1.

In FIG. 8, a further modified form of apparatus is shown at 10" that differs from the apparatus 10 principally by reason of the base/plate 20" being shifted in the direction of the arrow 68 away from the base 34" of the U-shaped portion 28".

The peripheral edge portion at 70 also is slightly different in that it does not have to have a shape conforming to that of the receptacle 46" defined by the U-shaped portion 28".

In FIG. 9, a further modified form of apparatus is shown at 10''' that is similar to the apparatus 10', with the primary distinction being that the base/plate 20''' is longer in a direction parallel to the length of the legs 30''', 32''' on the U-shaped portion 28''' and has three separate fastener openings 72*a*, 72*b*, 72*c*, each fully surrounded by the base/plate 20'''.

The opening 72*a* corresponds to the opening 60' with substantially the same configuration and location. The elongate/oval opening 72*b* corresponds to the opening 66 with its major axis extended further along the length of the legs 30''', 32'''. A second circular opening 72*c* is provided, with the elongate opening 72*b* located between the circular openings 72*a*, 72*c*.

In FIG. 10, a further form of apparatus is shown at 10$^{4'}$, with a base made up of separate, but like, plates/pieces 20*a*$^{4'}$, 20*b*$^{4'}$ with the piece 20*a*$^{4'}$ corresponding generally to the base/plate 20" in FIG. 8. The base piece 20*b*$^{4'}$ may abut to the base piece 20*a*$^{4'}$ or may be spaced therefrom.

In FIG. 11, a further modified form of apparatus is shown at 10$^{5'}$ with a configuration performing the function of the aforementioned "sled" device, described above. In this embodiment, a single elongate formed wire component 18$^{5'}$ defines a U-shaped mounting portion 28$^{5'}$ with separate base pieces 20*a*$^{5'}$, 20*b*$^{5'}$, spaced lengthwise of, and spanning between, the legs 30$^{5'}$, 32$^{5'}$ on the U-shaped portion 28$^{5'}$. Each base piece 20*a*$^{5'}$, 20*b*$^{5'}$ is preferably fixed to both legs 30$^{5'}$, 32$^{5'}$. Each of the base pieces 20*a*$^{5'}$, 20*b*$^{5'}$ has three leg openings 74 for suitable fasteners 22 that may be extended therethrough into bone at any one or more opening locations.

The "sled" apparatus configuration differs from the aforementioned buttress configurations primarily by reason of corresponding legs 40*a*$^{5'}$, 40*b*$^{5'}$ projecting at a smaller angle to the legs 30$^{5'}$, 32$^{5'}$ at the U-shaped portions 36*a*$^{5'}$, 36*b*$^{5'}$ so as to produce receptacles 62*a*$^{5'}$, 62*b*$^{5'}$ typically used to accommodate one or more bone fragments, to thereby captively maintain the bone fragments against a stabilizing bone part to which the U-shaped portion 28$^{5'}$ is fixed through the base pieces 20*a*$^{5'}$, 20*b*$^{5'}$. In addition, the legs 40*a*$^{5'}$, 40*b*$^{5'}$ engage the first bone part 12 as well as the second bone part 14.

In FIGS. 12-17, a further modified form of apparatus is shown at 10$^{6'}$ in a form Assignee identifies as its "Olecranon Sled" implant, shown operatively positioned with respect to a first bone part 12 and second bone part 14.

The apparatus has a unitary body 16$^{6'}$ with an elongate formed wire component 18$^{6'}$ fixed to/formed with a base 20$^{6'}$ as in prior embodiments.

A U-shaped mounting portion 28$^{6'}$ has spaced legs 30$^6$, 32$^{6'}$ which project in spaced relationship away from the base $20^{6'}$. The legs $30^{6'}$, $32^{6'}$ extend into U-shaped portions $36b^{6'}$, $36a^{6'}$, respectively having legs $40a^{6'}$, $40b^{6'}$. The U-shaped portions $36a^{6'}$, $36b^{6'}$ respectively define receptacles $62b^{6}$, $62a^{6'}$.

The legs $40a^{6'}$, $40b^{6'}$ extend through the first bone part 12 and into the second bone part 14, whereby a part of the first bone part 12 resides within the receptacles $62a^{6'}$, $62b^{6'}$. The base $20^{6'}$ overlies the second bone part 14 at a location spaced from a fracture site at F.

In this embodiment, the base $20^{6'}$ has similarly configured openings $80a^{6'}$, $80b^{6'}$. Exemplary opening $80a^{6'}$ has an elongate shape with a beveled edge $82a^{6'}$ which surrounds the opening $80a^{6'}$ at all but the edge region $84a^{6'}$ at one lengthwise end of the opening $80a^{6'}$.

An exemplary fastener $22^{6'}$ has a head 86 with a tapered region 88 extending to a threaded shank 90.

Figures 12, 13, 14, 15, 16, 17:
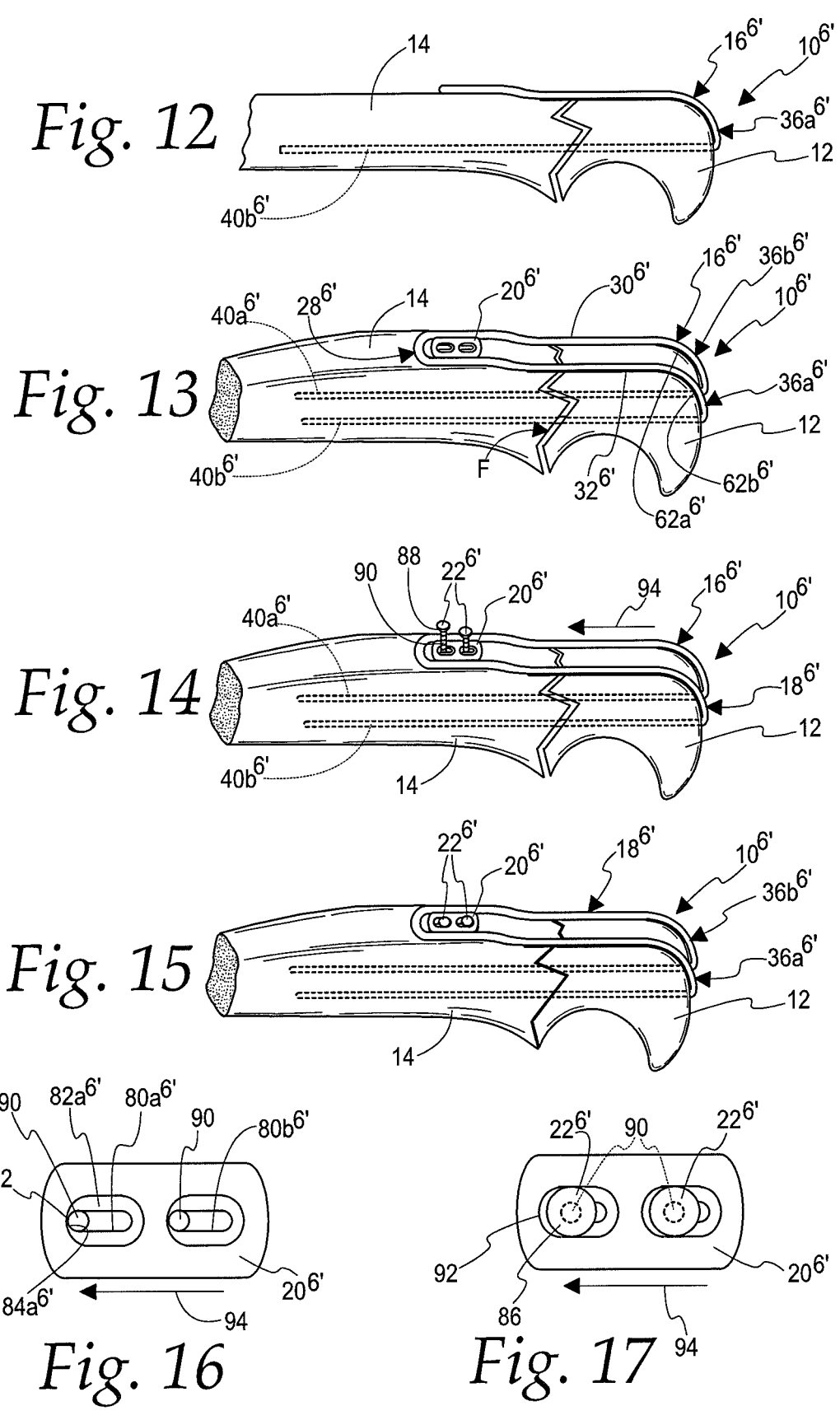
FIG. 12 is a side elevation view of first and second bone parts produced by a fracture at the olecranal region of a patient and with another form of the inventive apparatus in an operative position.
FIG. 13 is a perspective view of the components in FIG. 12.
FIG. 14 is a view as in FIG. 13 wherein fasteners are being directed into a base on the apparatus.
FIG. 15 is a view as in FIG. 14 wherein the fasteners are fully tightened as an incident of which the first bone part is drawn towards the second bone part.
FIG. 16 is an enlarged, plan view of a base on the apparatus in FIGS. 12-15 with fasteners initially being directed into openings on the base and heads of the fasteners removed.
FIG. 17 is a view as in FIG. 16 wherein the fasteners are tightened so as to cause the base to shift relative to the fasteners.

With the apparatus $10^{6'}$ operatively positioned, the shank 90 can be directed through the opening $80a^{6'}$ adjacent to the region $84a^{6'}$, as seen in FIG. 16. As the fastener $22^{6'}$ is advanced, the tapered region 88 encounters an edge 92 at the region $84a^{6'}$, whereupon a camming action occurs that wedges the base $20^{6'}$ in the direction of the arrow 94. As this occurs, the U-shaped portions $36a^{6'}$, $36b^{6'}$ draw the first bone part 12 towards the second bone part 14. Ultimately, the fastener $22^{6'}$ assumes the FIG. 17 position with the fastener $22^{6'}$ fully tightened and the wire shaped portions are "loaded" in tension so that residual restoring forces continue to bias the first bone part 12 towards the second bone part 14. The same type of fastener $22^{6'}$ can be used in the opening $80b^{6'}$.

Alternatively, only one of the openings $80a^{6'}$, $80b^{6'}$ may be required to allow the camming action.

Further details of the construction and intended use of the sled and buttress-type apparatus are provided in the Applicant's previously issued patents, identified above, and incorporated herein by reference.

As shown in flow diagram form in FIG. 18, using the above apparatus, a method of maintaining a position of a first bone part in relationship to a second bone part can be performed as follows.

As shown at block 100, an apparatus as described above is obtained including a unitary body made up of at least one elongate formed wire component and at least part of a base.

As shown at block 102, the apparatus is placed in an operative position wherein the at least one elongate formed wire component engages the second bone part.

As shown at block 104, with the apparatus in the operative position, a fastener is used to fix the base in relationship to the first bone part.

It is also contemplated that the fastener 22 can be directed into the second bone part as well as the first bone part to maintain a relationship with the apparatus.

As described in the incorporated prior art, various portions of the different apparatus may be directed into the second bone part 14, the first bone part 12, and/or engage externally in a bearing relationship.

Figures 18, 19, 20, 21, 22, 23, 24:
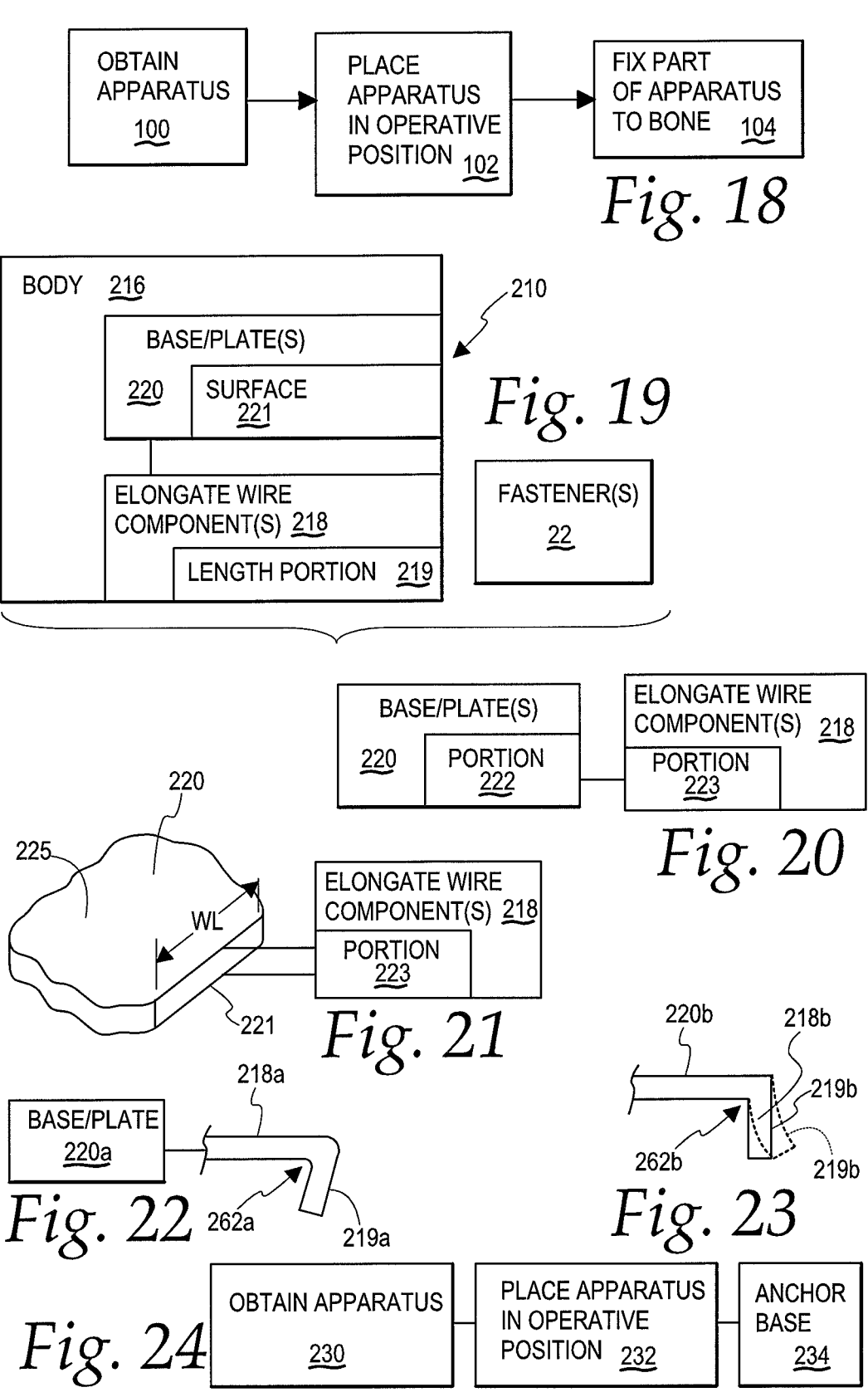
FIG. 18 is a flow diagram representation of a method of maintaining a position of a first bone part in relationship to a second bone part.
FIG. 19 is a schematic representation of another form of apparatus, according to the invention.
FIG. 20 is schematic representation showing additional details of the base/plate(s) and elongate wire component(s) as shown in FIG. 19.
FIG. 21 is a fragmentary perspective view of an exemplary form of base/plate, as shown in FIGS. 19 and 20, with an elongate wire component, shown in schematic form, welded thereto.
FIG. 22 is a partially schematic depiction of a base/plate and an elongate wire component, as shown in FIG. 19, wherein the elongate wire component defines a U-shaped receptacle.
FIG. 23 is a schematic depiction of a modified form of base/plate and elongate wire component, as in FIG. 19, wherein a U-shaped receptacle, as in FIG. 22, is defined cooperatively by the base/plate and elongate wire component.
FIG. 24 is a flow diagram representation of a method of maintaining a position of a first bone part relative to a second bone part, according to the invention and as performed using the apparatus in FIG. 19.

Another form of the inventive apparatus is shown schematically in FIG. 19 at 210 usable to maintain a position of a first bone part/fragment 12 relative to a second bone part/stable bone part 14.

The apparatus 210 consists of a unitary body 216 made up of at least one elongate wire component 218 with a length portion 219, and a base/plate(s) 220 with a surface 221.

The length portion 219 of the elongate wire component 218 is angled with respect to the base/plate surface 221.

In a preferred form, the elongate wire component 218 is permanently fixed to the base/plate 220. This permanent fixation may be effected by welding or by forming the elongate wire component(s) 218 and at least a part of the base/plate(s) 220 as one piece.

As with other embodiments, the apparatus 210 is configured to be placed in an operative position with the length portion 219 engaged with the first bone part/fragment 12 and the surface 221 of the base/plate 220 facing the second bone part/stable bone part 14.

The apparatus 210 may be provided in combination with one or more fasteners 22, each configured to be directed through the base/plate 220 and into the second bone part/stable bone part 14 to fix the base/plate 220 to the second bone part/stable bone part 14, to thereby maintain the apparatus 210 in an operative position, wherein part or all of the length portion 219 is engaged with the first bone part/fragment 12.

The apparatus 210 may take the same form as any of the different apparatus heretofore described, including apparatus constructed according to the schematic depiction in FIG. 1. Since any of the previously described apparatus may look substantially the same, whether made as previously described or as described below and through the schematic depiction in FIG. 19, there is no need to reproduce the prior Figures.

In most forms of the apparatus, the elongate wire components each has at least a portion that is more flexible than the associated base/plate. This allows the wire to be strategically loaded upon the implant being fixed in place so that residual forces thereby generated can be exerted on the bone parts. These residual forces may be bending forces, twisting forces, and/or lengthwise/axial forces (tensile or compressive) on deformed wire lengths that, with the apparatus in its operative position, tend to maintain a desired relationship between bone parts. The material of construction, gauge, and length of the elongate wire components dictates their axial strength, bending, and twisting characteristics.

In one preferred form, as mentioned above, the elongate wire components have a uniform cross-sectional shape and gauge over a majority, or an entirety, of the extent thereof. While this wire form is shown in all exemplary embodiments herein, this is not a requirement.

In one exemplary form of the apparatus 210, at least a portion of the base/plate 220 is formed as one piece with at least a portion of the at least one elongate wire component 218. For example, the apparatus 10 depicted in FIGS. 4 and 5, made consistent with the schematic depiction of the apparatus 210 in FIG. 19, may be made from a single piece, including part or all of the base 20 and part or all of the elongate formed wire component 18. This one-piece construction may be achievable by molding the apparatus 10, 210, forming the apparatus 10, 210 through a milling process, etc.

In one preferred form, the parts of the base/plate 20, 220 and elongate wire component 18, 218 are made from surgical grade metal. Use of a material other than metal is also contemplated. The apparatus 210 with the one-piece construction, and made with the exemplary basic design in FIGS. 4 and 5, may have the identical configuration of the apparatus 10 as depicted in FIGS. 4 and 5, or may have a different configuration over a part, or parts, thereof.

As noted, this one-piece construction may be utilized in all of the aforementioned apparatus. For purposes of simplicity, in the description and claims herein, in the one-piece construction, separate length portions of the elongate wire component will be considered to be part of the same elongate wire component, even if they are discrete/separate lengths joined through the base.

In an exemplary preferred form, as shown in FIGS. 6 and 7, the elongate wire component has at least one length portion, and as depicted two length portions, each extending away from the base 34' a distance greater than a largest areal dimension of the base 34'. In the depicted form, each of the length portions extends away from the base 34' a distance equal to more than two times the largest areal dimension of the base 34'.

In another exemplary preferred form, the elongate wire component has length portions extending, at least generally, oppositely away from the base 34'.

In an alternative form, within the schematic depiction of FIG. 18, the base/plate 220 and elongate wire component 218 may have portions 222, 223, respectively, that are welded together, as shown in FIG. 20.

In the embodiments described above, and without limitation, the base/plate 20/220 is shown with a substantially flat uniform thickness lending itself to being formed from a flat stock/sheet material. It is not necessary that the thickness be uniform or that the plate configuration be precisely flat, as shown between parallel flat surfaces. For example, the base/plate 20, 220 may be contoured to conform to a bone surface that the base/plate overlies. For purposes of simplicity, the plate configuration will be considered to be flat, even if it has a slight contour.

As shown in FIG. 21, in one form, the base/plate 220 has the aforementioned surface 221 facing in one direction and an oppositely facing flat surface 225. The portion 223 of the elongate wire component 218 is welded to the base/plate 220 at each of the surfaces 221, 225, thereby effectively resisting opposite bending forces tending to break the portion 223 of the elongate wire component 218 away from the base/plate 220.

Welding along only one of the surfaces 221, 225 is also contemplated.

As further depicted schematically in FIG. 20, the welding is effected continuously along a length WL of at least one, and preferably both, of the surfaces 221, 225.

In one preferred form, the welding is performed using a laser welding process.

In one form, the elongate wire component 218 defines a U-shaped receptacle, corresponding to the receptacles 62 previously described. As shown in FIG. 22, the elongate wire 218a by itself defines a U-shaped receptacle 262a into which at least part of the first bone part/fragment 12 resides with the apparatus 210 in its operative position. As shown schematically, the U-shaped receptacle 262a is spaced from the base/plate 220a.

In an alternative form, as shown in FIG. 23, the elongate wire component 218b defines a U-shaped receptacle 262b in conjunction with the base/plate 220b. Two exemplary different angled relationships between the length portion 219b and base/plate 220b are shown.

In both embodiments, each of the length portions 219a, 219b, respectively on the elongate wire components 218a, 218b, makes an angle with respect to its respective base/plate 220a, 220b.

As previously indicated, multiple elongate wire components 218 may be associated with each base/plate 220, as in embodiments described above. The additional wire component(s) may be welded to a base/plate, or part or all of the additional wire component(s) may be part of the one-piece construction.

It is also contemplated that the apparatus 210 may have multiple base/plates 220 corresponding to those as shown, for example, in FIG. 11.

Without limitation, at least part of the length portion 219 of each elongate wire component 218 is angled with respect to the exemplary surface 221, as shown in FIG. 21, that faces the second bone part/stable bone part 14 with the apparatus 210 in the operative position. The part of the elongate wire component 218 that is angled with respect to the base may be angled with respect to the base/plate 220 where it departs from the base/plate 220 or at a distance spaced from the base/plate 220. In each such configuration, the elongate wire component 218 will be considered to have a length portion projecting angularly away from the base/plate 220.

With the apparatus 210, one exemplary method of maintaining a position of a first bone part/fragment relative to a second bone part/stable bone part, according to the invention, may be carried out as shown in flow diagram form in FIG. 24.

As shown at block 230, an apparatus is obtained having a base/plate and at least one elongate wire component having at least a portion with a length projecting angularly away from the base/plate.

As shown at block 232, the apparatus is placed in an operative position wherein at least a portion of the length of the at least one elongate wire component engages the first bone part and a portion of the base/plate at least one of: i) bears against; and ii) is adjacent to the second bone part.

In one preferred form, as an incident of placing the apparatus in the operative position, at least a portion of the elongate wire is deformed by bending, twisting, and/or by being placed in lengthwise compression or tension, thereby generating residual forces in the elongate wire component tending to urge the second bone part towards/against the first bone part with the apparatus in the operative position.

As shown at block 234 with the apparatus in the operative position, the base is anchored to the second bone part to fix the apparatus in the operative position.

In one form, the anchoring of the base is effected through a fastener that extends through the base and into the second bone and in so doing cams the base to put at least a portion of the elongate wire component in tension so that the resulting residual forces urge the first bone part towards the second bone part. This is described above with reference to FIGS. 16 and 17.

While not required, at least a part of the base/plate and at least a part of the at least one elongate wire component are preferably made from metal and permanently connected, as by being welded together or made as one piece. As described above, the base is in the form of at least one plate, which may be substantially flat or otherwise configured.

With the plate having a substantially flat surface that faces the second bone part with the apparatus in the operative position, a length portion of the elongate wire component projects angularly with respect to the substantially flat surface of the plate.

The step of placing the apparatus in the operative position may involve causing the length portion of the at least one elongate component to engage the first bone part—by being placed against and/or by being directed into, the first bone part.

In one form, with the apparatus in the operative position, a U-shaped receptacle, defined at least in part by the elongate wire component, is situated so that a part of the first bone part resides in the U-shaped receptacle.

The foregoing disclosure of specific embodiments is intended to be illustrative of the broad concepts comprehended by the invention.

The invention claimed is:

1. A method of maintaining a position of a first bone part relative to a second bone part, the method comprising the steps of:
   a) obtaining an apparatus comprising a base and at least one elongate wire component having at least a portion with a length projecting angularly away from the base;
   b) placing the apparatus in an operative position wherein at least a portion of the length of the at least one elongate wire component engages the first bone part and a portion of the base at least one of: i) bears against; and ii) is adjacent to the second bone part and as an incident of placing the apparatus in the operative position causing at least a portion of the at least one elongate wire component to be deformed so that residual forces are generated in the at least one elongate wire component; and
   c) with the apparatus in the operative position, anchoring the base to the second bone part to fix the apparatus in the operative position,
   wherein at least a part of the base and at least a part of the at least one elongate wire component are made from metal and permanently connected,
   wherein the base is in the form of a plate.

2. The method of maintaining a position of a first bone part relative to a second bone part according to claim 1, wherein the plate is substantially flat.

3. The method of maintaining a position of a first bone part relative to a second bone part according to claim 2 wherein the plate is made from flat stock material.

4. The method of maintaining a position of a first bone part relative to a second bone part according to claim 1 wherein at least a portion of the at least part of the base and a portion of the at least part of the at least one elongate wire component are formed as one piece.

5. The method of maintaining a position of a first bone part relative to a second bone part according to claim 1 wherein the plate has a substantially flat surface that faces the second bone part with the apparatus in the operative position and the length of the portion of the at least one elongate wire component projects angularly with respect to the substantially flat surface of the plate.

6. The method of maintaining a position of a first bone part relative to a second bone part according to claim 5 wherein the step of placing the apparatus in the operative position comprises causing the at least portion of the length of the at least one elongate wire component to be directed into the first bone part.

7. The method of maintaining a position of a first bone part relative to a second bone part according to claim 1 wherein the at least one elongate wire component defines at least a part of a U-shaped receptacle and with the apparatus in the operative position at least a part of the first bone part resides in the U-shaped receptacle.

8. The method of maintaining a position of a first bone part relative to a second bone part according to claim 7 wherein the U-shaped receptacle is defined by only the at least one elongate wire component.

9. The method of maintaining a position of a first bone part relative to a second bone part according to claim 7 wherein the U-shaped receptacle is defined by the at least one elongate wire component in conjunction with the base.

10. The method of maintaining a position of a first bone part relative to a second bone part according to 1 wherein the at least one elongate wire component comprises additionally a second elongate wire component having a length portion projecting angularly away from the base, wherein at least a portion of the second elongate wire component is formed as one piece with at least a portion of the at least part of the base and a portion of the at least part of the at least one elongate wire component.

11. The method of maintaining a position of a first bone part relative to a second bone part according to claim 1 wherein the step of anchoring the base comprises directing a fastener through the base and into the second bone, the step of directing the fastener comprises camming the base with the fastener so that at least a portion of the residual forces are lengthwise forces in the at least portion of the at least one elongate wire component that urge the first bone part towards the second bone part.

12. An apparatus for maintaining a position of a first bone part relative to a second bone part, the apparatus comprising:
   a unitary body comprising: a) at least one elongate wire component; and b) a plate that has a first surface,
   wherein a length of at least a portion of the at least one elongate wire component is angled with respect to the first plate surface,
   wherein at least a part of each of the at least one elongate wire component and plate is made from metal,
   the at least one elongate wire component permanently fixed to the plate,
   the apparatus configured to be: a) placed in an operative position with the length of the at least a portion of the at least one elongate wire component engaged with the first bone part and the first surface of the plate facing the second bone part; and b) maintained in the operative position by fixing the plate to the second bone part,
   wherein at least a part of the at least one elongate wire component is configured to be deformed as an incident of the apparatus being placed in the operative position so that residual forces are generated in the at least one elongate wire component.

13. The apparatus for maintaining a position of a first bone part relative to a second bone part according to claim 12 wherein at least a portion of the at least part of the plate is formed as one piece with at least a portion of the at least one elongate wire component.

14. The apparatus for maintaining a position of a first bone part relative to a second bone part according to claim 13 wherein the at least one elongate wire component is welded to the plate at one of the first and second surfaces continuously along a length.

15. The apparatus for maintaining a position of a first bone part relative to a second bone part according to claim 12 wherein the plate is made from flat stock material.

16. The apparatus for maintaining a position of a first bone part relative to a second bone part according to claim 14 wherein a portion of the plate is laser welded to a portion of the at least one elongate wire component.

17. The apparatus for maintaining a position of a first bone part relative to a second bone part according to claim 12 wherein the plate has a second surface facing oppositely to the first surface and the at least one elongate wire component is welded to the plate at each of the first and second surfaces.

18. The apparatus for maintaining a position of a first bone part relative to a second bone part according to claim 17 wherein the at least one elongate wire component is welded to the plate along a length at each of the first and second surfaces.

19. The apparatus for maintaining a position of a first bone part relative to a second bone part according to claim 12 wherein the at least one elongate wire component defines at least a part of a U-shaped receptacle into which at least a part of the first bone part resides with the apparatus in the operative position.

20. The apparatus for maintaining a position of a first bone part relative to a second bone part according to claim 19 wherein the U-shaped receptacle is defined by only the at least one elongate wire.

21. The apparatus for maintaining a position of a first bone part relative to a second bone part according to claim 19 wherein the U-shaped receptacle is defined by the at least one elongate wire in conjunction with the plate.

22. The apparatus for maintaining a position of a first bone part relative to a second bone part according to claim 12 in combination with a fastener configured to be directed through the plate and into the second bone to maintain the apparatus in the operative position.

23. The apparatus for maintaining a position of a first bone part relative to a second bone part according to claim 12 wherein the at least one elongate wire component comprises additionally a second elongate wire component having at least another portion with a length and the length of the at least another portion of the second elongate wire component is angled with respect to the first plate surface.

24. The apparatus for maintaining a position of a first bone part relative to a second bone part according to claim 12 wherein the plate is formed from a flat stock material.

25. The apparatus for maintaining a position of a first bone part relative to a second bone part according to claim 12 wherein the unitary body comprises a second plate.

\* \* \* \* \*